United States Patent [19]

Owen et al.

[11] 3,966,586

[45] June 29, 1976

[54] METHOD FOR UPGRADING HEAVY PETROLEUM TYPE STOCKS

[75] Inventors: Hartley Owen, Belle Mead; Paul B. Venuto, Cherry Hill, both of N.J.

[73] Assignee: Mobil Oil Corporation, New York, N.Y.

[22] Filed: July 31, 1974

[21] Appl. No.: 493,445

[52] U.S. Cl. ................................. 208/120; 208/44; 208/78; 208/251 R; 208/254 R; 260/614 A; 260/668 R
[51] Int. Cl.² ................. C10G 11/04; C10G 37/06; B01J 8/24; B01J 29/28
[58] Field of Search .............................. 208/120, 78

[56] References Cited
UNITED STATES PATENTS

| | | | |
|---|---|---|---|
| 2,211,944 | 8/1940 | Andrews et al. | 208/121 |
| 2,456,584 | 12/1948 | Gorin et al. | 260/668 |
| 3,036,134 | 5/1962 | Mattox | 260/614 |
| 3,529,033 | 9/1970 | Frilette et al. | 260/682 |
| 3,728,408 | 4/1973 | Tobias | 260/668 C |
| 3,758,403 | 9/1973 | Rosinski et al. | 208/120 |
| 3,856,873 | 12/1973 | Burress | 260/672 T |

*Primary Examiner*—Delbert E. Gantz
*Assistant Examiner*—G. E. Schmitkons
*Attorney, Agent, or Firm*—Charles A. Huggett; Carl D. Farnsworth

[57] ABSTRACT

Heavy hydrocarbon feeds are dispersed in solvent ethers and product recycle fraction prior to catalytic cracking thereof with acidic compositions comprising particular crystalline zeolite catalyst composition. The solvent ethers are provided by reacting process olefins with methanol to produce low and high molecular weight ethers separately.

10 Claims, 1 Drawing Figure

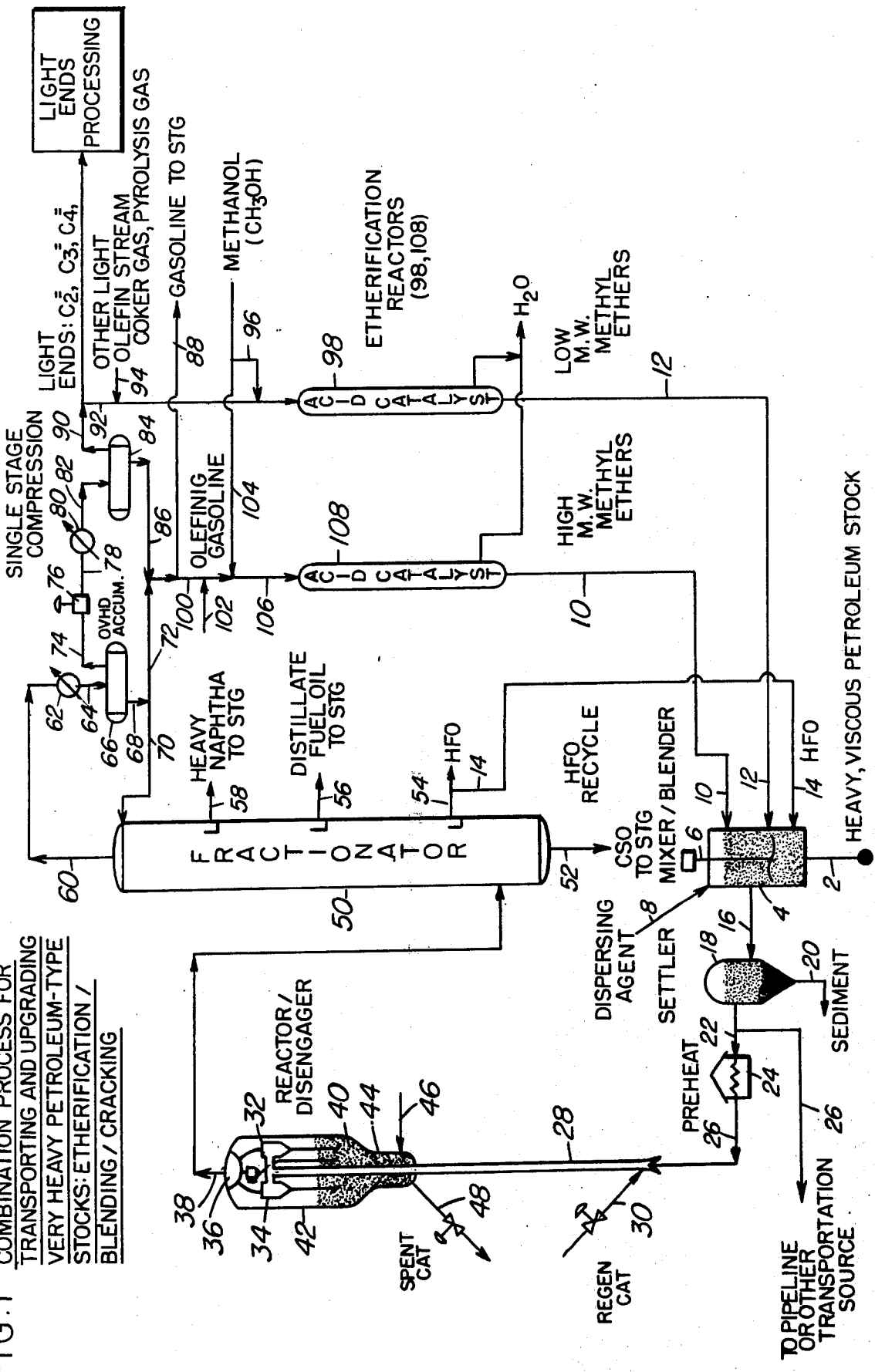

METHOD FOR UPGRADING HEAVY PETROLEUM TYPE STOCKS

BACKGROUND OF THE INVENTION

Petroleum refiners are currently faced with a need to transport and process very high molecular weight, heavy often hydrogen deficient feedstocks. Examples of these are bitumens, syncrudes from tar sands, etc. Such materials are often highly viscous, tarry, and have high pour points; in fact, some of these are actually solid. Thus transportation of these materials are recovered, particularly pipelining, is difficult, if not impossible, particularly in cold climates.

Very limited methods are available to transport and process really heavy, very high pour point, viscous petroleum type materials. Solvent deasphalting, visbreaking, pyrolysis, etc. have been proposed as means of initiating the downstream processing of these materials, but these procedures are costly, and may result in the degradation of substantial amounts of hydrocarbon to products of low value, or still not product materials of sufficient fluidity to flow well in pipelines.

The present invention is concerned with rectifying many of the prior art problems for processing heavy stocks as herein defined.

SUMMARY OF THE INVENTION

In the present invention, heavy residual hydrocarbon stocks such as those herein defined are dissolved, intimately mixed, or dispersed in a strong solvent containing a mixture of methyl ethers, and either transported to another location for further processing or upgraded on site by catalytic cracking. The mixture is thereby upgraded to produce products of quality and yield superior to those formed in the absence of the methyl ether solvent. The cracking reaction may occur in the presence of a hydrogen activating function or after exposure of the mixture of methyl ether solvent plus heavy stock to a catalyst with a hydrogen activating function. The methyl ether solvent is derived from reaction of cracking process-derived olefins ($C_2$ through $C_{11}$ or $C_{12}$) and/or other $C_2$ to $C_{11}$ or $C_{12}$ olefins with methanol in the presence of an etherification catalyst.

By heavy stock it is intended to include any material that boils higher than conventional gasoline end point material, i.e., about 11–12 C-number or higher. Examples of such heavy stocks include distillate gas oils, cycle oils, heavy vacuum gas oils, atmospheric residua, syncrydes from shale oil, tar sands or coal, bitumens, or even pulverized coal itself. It may also include any heavy crude from primary, secondary or tertiary recovery systems and from conventional or off-shore oil fields.

The catalyst employed in the processing concept of this invention broadly includes any acidic composition, most preferably a solid, such as a zeolitic cracking catalyst. Preferred catalyst compositions contain a portion of one or more crystalline zeolite compositions intimately dispersed in a matrix. Zeolites ZSM-5 (and ZSM-5 type) and mordenite (and mordenite-type, or dealuminized mordenity, or TEA-mordenite) are preferred. They may be used alone or in the presence of a faujasite-type component such as REY, etc. It is preferred to employ a dual component cracking catalyst comprising ZSM-5 or mordenite-types and REY type zeolites.

The catalyst may have a hydrogen-activating function which will aid in the redistribution or transfer of hydrogen. Such catalysts are known as hydrogen dissociation, hydrogen activation, or hydrogenation catalysts. The catalyst with a hydrogen-activating function may or may not contain a metal function. Some of the preferred metal functions include Pt, Ni, Fe, Re, W, Mo, Co, Th, Cr, Ru, V or Cu. Catalyst functions known in the art to catalyze the Fischer-Tropsch reaction, the water gas shift reaction, and olefin disproportionation may be particularly preferred.

By "other $C_2$-$C_{11}$/$C_{12}$ olefins" is meant any other refinery stream that contains olefins, i.e. coker off gas, coker naphtha, pyrolysis gasoline, etc.

By etherification catalyst is meant any catalyst capable of etherifying alcohols or catalyzing the addition of an alcohol to an olefin to form an ether, viz.,

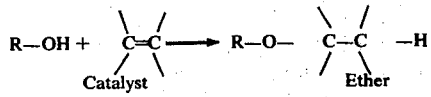

Such catalysts are available and known in the art, and may include mineral acids, supported acids, macroreticular ion exchange resins, amorphous crystalline aluminosilicates, alumina, etc. The etherification can be done in fixed bed, stirred tank, or any practical reactor system; conditions are generally mild in terms of temperature and pressure. Generally the temperature is within the range of 30° to 300°F. and the pressure is within the range of 50 to 200 psig.

Some more specific aspects and advantages of the improved processing concepts of the present invention are provided below.

It makes use of methanol, a product which is expected to be available in quantity, either as a transportable product from overseas natural gas conversion processes or as a product from large scale coal, shale, or tar sand gasification.

Cracking of the heavy stock in the presence of the ether solvent is associated with increased gasoline yield and/or quality (including higher octane and improved volatility), and increased yields and/or quality of fuel oils — including improved burning quality and lower levels of potential polluting impurities, which improvements are not obtained in the absence of the ether solvent. This new process concept allows for less severe reforming requirements. Because of the improvement in fuel oil quality, lower hydrotreating requirements and severities are also permitted.

Mixing (dissolving, dispersing, solubilizing, etc.) the heavy stock in the methyl ether solvent provides improvements in viscosity, pour point, gravity, etc., allowing the heavy stock to be easily transported, pipelined, or processed on site. The wt./wt/ ratio of methyl ether rich solvent which may or may not contain aromatics, paraffins, etc., to heavy stock can vary over a relatively wide range, i.e. from about 0.01–20, with about 0.1–6 being preferred. The exact ratio will depend upon how refractory the stock to be processed is. The mixture of methyl ethers, particularly in combination with aromatics derived from the gasoline fractions), constitutes a strong solvent for polymers and high molecular weight polar molecules: this solvent mixture is "balanced", i.e. it covers a wide molecular weight range of ethers, etc. i.e. $C_2$-$C_{12}$ in carbon number. This solvent system provides good access to and solvates effectively rigid, 3- dimensional polynuclear aromatics, sulfur and nitrogen heterocycles, resins, asphaltenes, etc., thereby making them more "liquid-like", more accessible to catalyst sites during the catalytic cracking phase, and places the methyl ether, which is a "carbon/hydrogen-contributing fragment" in close proximity to the high molecular weight hydrogen-deficient moieties of the charge. Thus synergistic hydrogen transfer effects may be expected to occur in addition to the solvent behaving like a "cutter stock".

It is contemplated employing a dispersing agent such as particularly a nonionic type in small amounts to aid in the intimate mixing of methyl ether solvent with heavy stock.

In addition, a small amount of stock with high basic nitrogen (such as a shale oil fraction) may be added, which polar nitrogen-containing material may aid in the dissolution/solvation/upgrading of heavy stocks, especially pulverized coal.

When a particularly strong solvent is required, it is contemplated relying upon the synthesis of powerful ketonic solvents via the Oxo reaction using FCC regenerator CO. Such ketonic solvents could also be utilized in a dewaxing operation if so desired.

Solvent deasphalting of the heavy stock or selected streams used in the refinery scheme may also be practiced as warranted.

Since the whole crude is cracked in the combination operation of this invention (without prior demetalation) a certain amount of $H_2$-gas is formed: this gaseous $H_2$ can efficiently be used for hydrotreating part or all of certain heavy streams, and/or as feed for the Oxo unit; thus the need to build a large and expensive $H_2$ plant may be considerably reduced.

A particular advantage of the processing arrangements of this invention is that they occur at low pressures (i.e. at pressures commonly employed in current catalytic cracking operations or slightly higher). It allows highly efficient contact of relatively inexpensive "carbon/hydrogen-contributing fragments" with a spectrum of feed molecules of widely differing molecular weights in the presence of high surface area cracking and/or hydrogen-activating functions, thus maximizing facile intermolecular hydrogen-transfer interactions and subsequent cracking reactions, and minimizing problems due to diffusion/mass transport limitations and/or heat transfer. While this process is preferred in riser or dilute phase beds, it is also applicable in fluidized dense beds, fixed beds, or moving bed operations. Single or multistage operations can be utilized. Further, the catalyst functions referred to above, may be on the same catalyst particle, or on different catalyst particles.

The processing combinations of the present invention may also be modified to include any combination of the following concepts:

That a provision is made for the efficient recycle of unreacted "carbon/hydrogen-contributing fragments" such as methanol, dimethyl ether, light olefins etc. or other convertible materials.

A plurality of separate riser reactors may be provided for upgrading light ends, gasoline-range materials, etc., wherein temperature, catalyst/oil ratio, residence time, catalyst activity/selectivity-type can be varied to meet the requirements of a particular fraction (or product specification).

It is contemplated providing for the cascade or recycle of coke-deactivated catalyst to regulate catalyst/oil ratio or catalyst activity/selectivity in a desired conversion zone.

Provision is made for multiple injection of ether solvents or other "carbon/hydrogen-contributing fragments" of substantially any molecular weight range along the riser(s)/reactor length.

A catalyst regeneration system is contemplated and may be provided if desired wherein a particle density gradient (between two catalyst types of different density) is established in a regenerator, and regenerated catalyst from each of the two (density) zones is returned separately to various sections of the risers.

The processing combinations of this invention may be modified to provide for using different catalysts in the separate riser systems or in separate stages of a single riser reactor in combination with a common or separate catalyst regeneration system.

BRIEF DESCRIPTION OF THE DRAWINGS

The figure is a schematic drawing in elevation of a combination process for upgrading heavy petroleum materials in combination with etherification of product components, blending and catalytic cracking.

DISCUSSION OF SPECIFIC EMBODIMENTS

Referring now to the figure by way of example, a heavy viscous petroleum material such as syncrude obtained from tar sands as hereinbefore defined is introduced to the process by conduit 2 to a mixer or blender 4. The blender 4 is provided with a mixing device or stirrer 6. A dispersing agent, defined above, may be introduced by conduit 8. Also a high molecular weight ether product of the process may be introduced by conduit 10, a low molecular weight ether product of the process may be introduced by conduit 12 and heavy fuel oil product may be introduced by conduit 14. The blended mixture formed in zone 4 at a temperature within the range of 30° to 300°F. is then passed by conduit 16 to a settling vessel 18 wherein a sediment is separated from liquid material and withdrawn from the bottom thereof by conduit 20. There may be a plurality of settling vessels provided in parallel and/or sequential arrangement. The liquid material separated in settling zone 18 is passed by conduit 22 to a preheat furnace 24 wherein it is heated to a temperature of about 300°F. to about 800°F. A portion of the liquid in conduit 22 may be withdrawn by conduit 26 for passage to a pipeline or other transportation facilities available for the purpose.

The preheated syncrude with added materials as above defined is then passed by conduit 26 to the lower portion of a riser cracking zone 28 provided with hot regenerated catalyst at a temperature in the range of 1000°F. to 1400°F. by conduit 30. In riser 28, the syncrude feed is converted with a crystalline zeolite containing cracking catalyst under conditions including a temperature within the range of 800°F. to about 1100°F. at a hydrocarbon residence time within the range of 1 to 20 seconds. The catalyst to oil ratio employed will vary considerably depending upon reaction conversion conditions desired, the feed composition, the catalyst temperature and the feed preheat temperature. Furthermore, the type of catalyst employed will influence the catalyst to oil ratio employed, that is, whether a single or dual cracking component catalyst is employed.

The suspension of catalyst in charged hydrocarbons passed through the riser conversion zone is separated by discharge through a plurality of cyclonic separators 32 and 34 each of which may be a plurality of sequentially arranged cyclonic separators attached to or separated from the discharge end of the riser conversion zone. In the cyclonic separators, catalyst particles are separated from hydrocarbon vapors. The hydrocarbon vapors are passed by conduit means connecting the cyclones to the plenum chamber 36 and eventual removal therefrom by conduit 38. Catalyst separated by the cyclonic means is passed by cyclonic separator diplegs to a bed of catalyst 40 collected in the lower portion of vessel 42 housing the upper end of the riser and the cyclonic separating means. A stripping section 44 comprising a downwardly extending smaller diameter portion of vessel 42 is in open communication therewith for downward flow of collected catalyst and upward flow of stripping gas introduced by conduit 46.

Stripped catalyst is withdrawn from a lower portion of the stripping section 44 by conduit means 48 for transfer to a catalyst regeneration zone not shown. The catalyst is regenerated by removing deposited carbonaceous material by burning with an oxygen containing gas thereby heating the catalyst to a temperature within the range of 1000°F. to about 1400°F. and more usually above 1200°F. Regeneration of the catalyst may be accomplished by any one of the more modern techniques now known and used for regenerating relatively low coke producing crystalline zeolite conversion catalysts.

The vaporous products of the hydrocarbon conversion operation removed from vessel 42 by conduit 38 are passed to a fractionation tower 50 for separation into desired products. In fractionation tower or zone 50 a separation is made for the recovery of a clarified slurry oil (CSO) by conduit 52, a heavy fuel oil (HFO) by conduit 54, a light fuel oil or light cycle oil (LCO) by conduit 56, and a heavy naphtha fraction withdrawn by conduit 58. Materials lower boiling than the heavy naphtha fraction are withdrawn from an upper portion of the tower by conduit 60.

The materials withdrawn by conduit 60 at a temperature of about 350°F. depending on pressure are cooled in cooler 62 to a temperature of about 100°F. before passage by conduit 64 to an overhead accumulator drum 64 wherein a separation is made with a gaseous phase and a liquid phase. Drum 64 may be retained at a pressure within the range of 15 to 30 psig. The separated liquid phase is withdrawn from drum 68 by conduit 68 with a portion thereof passed by conduit 70 to the upper portion of tower 50 as reflux. The remaining portion of the recovered liquid is withdrawn by conduit 72 and used as hereinafter described.

Vaporous material separated in drum 66 is withdrawn by conduit 74 and passed to a compressor 76 wherein the pressure of the vaporous phase is raised to about 75 psig. The compound vaporous phase is passed by conduit 78 to cooler 80 wherein its temperature is reduced to about 100°F. before passage by conduit 82 to accumulator drum 84. In drum 84 a separation is made between vaporous material and liquid material. The separated liquid at a pressure of about 75 psig is removed from the drum by conduit 86 communicating with conduit 72. A pressure relief valve is provided in conduit 86. The condensed liquid in conduits 72 and 86 is combined and may be withdrawn in part by conduit 88 as gasoline product of the combination operation.

The vaporous material separated in pressured drum 84 is removed therefrom by conduit 90 and comprises lights ends materials such as $C_4$ and lower boiling olefins. A portion of these light ends may be passed to light ends recovery and processing by method not shown or a part of this invention. A portion of the light ends in conduit 90 withdrawn by conduit 92 is combined with other light olefins available from coking operations, pyrolysis gas, etc., introduced by conduit 94. The mixture of light olefins thus formed is combined with methanol or other low boiling alcohols introduced by conduit 96 and passed to a reaction zone 98 identified as an etherification reaction zone.

A portion of the light gasoline product of this process recovered by conduits 72 and 86 is withdrawn by conduit 100 and is combined with other available light olefinic gasoline such as obtained from coking, pyrolysis operations, etc., introduced by conduit 102. This mixture is combined with methanol or other low boiling alcohols introduced by conduit 104. This mixture is then passed by conduit 106 to an etherification reaction zone 108.

The light olefinic materials passed to the process by conduit 94 may be obtained from the product gases of steam reforming, thermal cracking, coking, visbreaking as well as from in situ recovery of in ground heavy oil by the technique of fire flooding. In etherification reaction zones 98 and 108, the materials charged as above identified are converted to methyl ethers or a distribution of products derived therefrom. That is, the materials charged to zone 98 are converted to low molecular weight methylethers and the materials charged to zone 108 are converted to high molecular weight methyl ethers. Low molecular weight methyl ethers are represented by structures such as $CH_3$-O-$CH_2$-$CH_3$, $CH_3$-O-$CH(CH_3)_2$, $CH_3$-O-$C(CH_3)_3$, etc.

High molecular weight methyl ethers are represented by structures such as $CH_3$-O-$C_6H_{13}$, $CH_3$-O-$C_8H_{17}$, $CH_3$-O-$C_{12}H_{23}$, etc.

In etherification zones 98 and 108, the operating temperature is maintained within the range of 30°F. to about 300°F. and preferably is less than 200°F. The operating pressure on the other hand is preferably less than 200 psig and more usually is retained within the range of 50 to 100 psig. The pressure is preferably autogenous at the temperature employed. In the etherification reaction it is preferred to maintain an excess of the alcohol to the olefin charged of about 2 to 1 but the ratio may vary from 0.1/1 to 5/1. The catalyst employed may be dilute sulfuric acid, organic sulfonic acids, supported mineral acids, promoted Lewis acids such as aluminum chloride and supported Lewis acids. Also macroreticular organic ion exchange resins containing acid functions such as sulfonic acid groups may be employed. The reaction zone may be operated as batch, stirred tank continuous flow and continuous flow fixed bed arrangements. It is particularly desirable to avoid high temperatures, preferably less than 300°F. and any unreacted alcohols may be recovered and recycled in the operation. When using the macroreticular resin catalyst it is preferred to employ a fixed catalyst bed continuous flow arrangement relying upon two or more beds of catalyst in parallel flow arrangement. A water product of the process is separated from formed ethers and removed from the process by any suitable known technique. In the arrangement of the figure the high molecular weight methyl ether formed in zone 108 is withdrawn by conduit 10 and used as above discussed. The low molecular weight methyl ether is withdrawn from zone 98 by conduit 12 and used as above discussed.

In the combination operation of this invention it is contemplated supplying a plurality of riser reaction zones with catalyst obtained from a common regeneration zone for processing different feed components of the process. That is, it is contemplated separately converting a portion of the low and high molecular weight ethers in separate riser reactors particularly with a ZSM-5 type crystalline zeolite conversion catalyst. In this combination operation the heavy residual feed is combined with the solvent materials as specifically discussed above with respect to the figure and restructuring of a portion of the formed ethers to desired products including gasoline boiling products is particularly enhanced. As mentioned above, the catalyst particularly comprises a zeolite such as ZSM-5 and ZSM-5 type, mordenite and mordenite type or dealuminized mordenite are preferred catalysts. However, these catalysts may be used alone or with an amorphous support providing some degree of cracking activity or they may be used in the presence of an "X" or "Y" faujasite crystalline zeolite, preferably REY (rare earth exchanged "Y" faujasite) in which combination the REY component is in minor proportion and the zeolites are supported by a matrix material comprising relatively catalytically inert one or more inorganic oxide materials.

DISCUSSION OF SPECIFIC EMBODIMENTS

Solubility and Catalytic Reaction of Tar Sand Derived Heavy Stock

Water and Sand Removal.

A sample was obtained of Athabasca tar containing sand and about 40% water in intimate admixture with the black, viscuous bitumen. The sample (about 100g) was subjected to azeotropic distillation with xylene (reflux temperature of ~ 280°–285°F) and a large part of the entrained water removed in this manner; the remaining water and a small amount of sand were removed by centrifugation. The xylene remaining in the tar was then removed by careful atmospheric distillation.

Solubility Studies on Tar Sand-Derived Hydrocarbon.

Solubility of the black, viscous tarry hydrocarbon (API 13.2° at 60°F) was tested in a number of ether solvents chosen to simulate the solvent environment that could be obtained by reaction of olefinic FCC gasoline and FCC light olefin streams with methanol over acid catalysts to form mixtures of ethers of various molecular weights.

EXAMPLE 1

Water - and sand-free tar sand oil (0.21g) was contacted with tert-butyl methyl ether (2.0 ml) at 80°F (~1 atm) with gentle shaking in a vial. The black oil dissolved rapidly, forming a brown solution, with only a few very small flocculent specks adhering to the side of the vial.

EXAMPLE 2

Water - and sand-free tar sand oil (0.57g) was contacted with a solution made up of tert-butyl methyl ether (1.0 ml), ethylene glycol dimethyl ether, $C_4H_{10}O_2$ (1.0 ml) and diethylene glycol dimethyl ether, $C_6H_{14}O_3$ (1.0 ml) at 80°F (~1 atm) in a vial. Dissolution of black oil to form a deep brown, clear solution occurred rapidly.

EXAMPLE 3

Water - and sand-free tar sand oil (0.36g) was contacted with a solution in a vial containing 1.0 ml each of the high molecular weight ethers di-hexylether ($C_{12}H_{26}O$) and di-octyl ether ($C_{16}H_{34}O$) at 80°F (~1 atm). After shaking gently, the black oil slowly and completely dissolved, forming a dark brown solution.

These experiments show that heavy petroleum-type oils such as those derived from Athabasca tar sands are capable of dissolving in ethers and mixed ethers similar to those derived from reaction of FCC olefinic fractions with methanol. A typical reaction of this type is the reaction of isobutylene with methanol to form tert-butyl methyl ether, i.e.

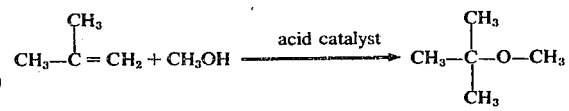

The above experimental date suggest that even high molecular weight ethers, such as those formed from gasoline range olefins plus methanol, will be excellent solvents for such heavy oils. The solublizing power ethers relates to the presence of the group R—O—R, which oxygen function has high solvating ability. In practical refinery operations, where FCC gasoline is treated with methanol to produce methyl ethers from the gasoline olefins, the gasoline aromatics will also assist in dissolution of the heavy oil.

EXAMPLE 4

Pilot Plant Riser FCC Conversion of Tar Sand Dissolved in tert-Butyl Methyl Ether The water - and sand-free tar sand oil used showed these typical inspections: API gravity (60°F), 13.2; refractive index (70°C), 1.52; molecular weight, ~ 625; wt. % hydrogen, 11.0; wt. % sulfur, 2.69; wt. % total nitrogen, 0.34; metals (ppm): Ni(57), V(174), Fe(891); boiling range, ~ 300°F +. The charge stock was Athabasca type. Tert-butyl methyl ether was commercially obtained.

Black water - and sand-free tar sand oil (18.2g) was intimately mixed with and dissolved in tert-butyl methyl ether (111.3g). This corresponds to a solution of 14.02 wt. % tar sand oil in the ether; the molar ratio of tert-butyl methyl ether to tar sand oil was 43.5. The feed mix was pumped to the inlet of the feed preheater of a 30 ft. bench scale riser FCC unit. Stocks were intimately mixed in the feed preheater at 790°F, and then admitted to the riser inlet, where hot (1094°F) catalyst (Ashland Equilibrium Test No. 3, burned-white, 67.5 FAI) was admitted and catalytic reaction allowed to occur. Riser reactor inlet and mix temperature were 1000°F, ratio of catalyst to oil (Oil = Tar sand oil plus ether) was 7.23, catalyst residence time was 2.9 sec., riser inlet pressure was 30 psig, and ratio of catalyst residence time to oil residence time (slip) was 1.24. Riser effluent then passed through a stream stripping chamber, and gaseous effluent was separated from spent catalyst (0.893 wt. % carbon) and the gaseous and liquid products collected, separated by distillation and analyzed. This run is number H-655. Date for operating conditions and mass balance are shown in Tables 1 and 2 respectively.

The results in Table 2, based on amount of tar sand oil charged and amount of cycle oil remaining, show that substantial quantities of refractory tar sand oil were converted to useful products, and that the ether solvent, by co-reacting, also contributed to the formation of gasoline and other useful fuel products. The very large amounts of butene and isobutane are derived in large part from reaction of the tertbutyl methyl ether; butene could be recycled to the process again, or the total $C_4^=$ - stream sent to alkylation. Thus these results provide a practical method of handling, transporting, and converting a highly refractory, heavy, highly aromatic tar sand oil.

TABLE 1

REACTION OF TAR SAND OIL/TERT-BUTYL METHYL ETHER MIX OVER A 15 PERCENT REY CRYSTALLINE ZEOLITE CATALYST

| Reaction Conditions | H-655 |
|---|---|
| Reactor Inlet Temp., °F | 1000 |
| Oil Feed Temp., °F | 790 |
| Catalyst Inlet Temp., °F | 1094 |
| Catalyst/Oil (wt/wt) Ratio | 7.23 |
| Catalyst Residence Time, Sec. | 2.9 |
| Reactor Inlet Pressure, PSIG | 30 |
| Moles of Product/Mole Feed (Ex Coke) | 1.718 |
| Oil Partial Pressure, Inlet, psig | 37.7 |
| T mix, °F | 1016 |
| Carbon, Spent Catalyst, % wt. | .893 |
| Sulfur, Spent Catalyst, % wt. | — |
| Nitrogen, spent Catalyst, % wt. | — |
| Slip Ratio | 1.24 |
| Solvent | tert-Butyl Methyl ether |
| Solvent wt. % of Tar Sand Oil | 613.1 |
| Molar Ratio, Solvent/Tar Sand Oil | 43.5 |

TABLE 2

Product Selectivities (Basis: 100g Total Feed)

| Run | |
|---|---|
| Charge In | |
| Tar Sand Oil, g | 17.0 |
| tert-Bu-Me-Ether, g | 83.0[b] |
| Total, g | 100.0 |
| Products Out, g | |
| $C_5^+$ Gasoline[a] | 21.4 |
| Total $C_4$ | 54.7 |
| Dry Gas | 8.3 |
| Coke | 8.4 |
| Cycle Oil[a] | 7.2 |
| Light Product Breakdown, g. | |
| $H_2S$ | .07 |
| $H_2$ | .14 |
| $C_1$ | 4.06 |
| $C_2^=$ | .00 |
| $C_2$ | .74 |
| $C_3^=$ | 1.93 |
| $C_3$ | 1.35 |
| $C_4^=$ | 33.09 |
| i-$C_4$ | 21.64 |
| n-$C_4$ | .01 |
| $C_5^=$ | 4.11 |
| i-$C_5$ | 1.75 |
| n-$C_5$ | 1.03 |
| Recovery, wt. % of feed | 92.1 |
| $H_2$ - Factor | 18 |

[a]Cut point between gasoline and cycle oil is 430°F TBP.
[b]Basis on complete removal of $H_2O$ from tert-butyl methyl ether during reaction, i.e. on "$C_5H_{10}$" basis. Only small amounts of methanol, dimethyl ether and CO were found in gaseous products.

Having thus generally described applicants' invention and discussed specific embodiments in support thereof, it is to be understood that no undue restrictions are to be imposed by reason thereof except as defined by the following claims.

We claim:

1. A method for upgrading heavy hydrocarbon feeds which comprises,
   combining the heavy hydrocarbon feed with one or more lower boiling components selected from the group comprising low and high molecular weight methyl ethers, and a heavy cycle oil product of the operation,
   converting the heavy hydrocarbon feed combined with said lower boiling component by contact with a crystalline zeolite containing conversion catalyst at a temperature within the range of 800°F. to about 1100°F.,
   separating catalyst from the products of said conversion operation,
   separating the products of said conversion operation into heavy fuel or recycle oil, light cycle oil, heavy naphtha, a light gasoline product and a gaseous product comprising $C_4$ and lighter olefins,
   converting light olefin product of the process admixed with methanol to a low molecular weight methyl ether,
   converting a portion of the gasoline product admixed with an olefin rich light naphtha and methanol to form high molecular weight methyl ethers and
   using the methyl ethers thus formed as a solvent for the heavy hydrocarbon feed to be processed.

2. The method of claim 1 wherein the crystalline zeolite containing catalyst comprises one or more components selected from the group comprising ZSM-5 type crystalline zeolite, mordenite type crystalline zeolite, dealuminized mordenite used alone or in combination with an "X" or "Y" faujasite crystalline zeolite.

3. The method of claim 1 wherein the heavy hydrocarbon feed is selected from the group comprising distillate gas oils, cycle oils, heavy vacuum gas oils, atmospheric residua, and syncrudes from shale oil, tar sands and coal.

4. The method of claim 1 wherein the crystalline zeolite conversion catalyst comprises a dual component catalyst comprising ZSM-5 and rare earth exchanged "Y" faujasite.

5. The method of claim 1 wherein the crystalline zeolite conversion catalyst comprises a mixture of mordenite and rare earth exchanged "Y" type crystalline zeolites.

6. The method of claim 1 wherein the crystalline zeolite is provided with a hydrogenating metal component.

7. The method of claim 1 wherein the ether solvent is derived from reaction of cracking derived olefins $C_2$ through $C_{12}$ alone or in combination with olefins derived from coker off gas, coker naphtha and pyrolysis gasoline with methanol in the presence of an etherification catalyst.

8. The method of claim 1 wherein mixing of the low and high molecular weight ethers with the heavy hydrocarbon feed is accomplished in the presence of a nonionic dispersing agent.

9. The method of claim 1 wherein conversion of the dissolved heavy hydrocarbon feed is practiced in the presence of methanol.

10. The method of claim 1 wherein the heavy hydrocarbon feed is an oil obtained from tar sands.

* * * * *